US008180575B2

(12) United States Patent
Esteban et al.

(10) Patent No.: US 8,180,575 B2
(45) Date of Patent: May 15, 2012

(54) PROCESS AND SYSTEM FOR ON-LINE AND IN SITU COUNTING OF CELLS IN A BIOLOGICAL CULTURE MEDIUM

(75) Inventors: Geoffrey Esteban, Nimes (FR); Bruno Luong, Nimes (FR); Frédéric Ossart, Langlade (FR)

(73) Assignee: Nanotec Solution, Nimes (FR)

( * ) Notice: Subject to any disclaimer, the term of this patent is extended or adjusted under 35 U.S.C. 154(b) by 646 days.

(21) Appl. No.: 12/135,743

(22) Filed: Jun. 9, 2008

(65) Prior Publication Data

US 2008/0312843 A1    Dec. 18, 2008

(30) Foreign Application Priority Data

Jun. 15, 2007   (FR) ..................................... 07 04302

(51) Int. Cl.
*G01N 33/48*   (2006.01)

(52) U.S. Cl. ...................................... 702/21; 73/335.04

(58) Field of Classification Search .................... 702/19, 702/20, 21, 29, 75, 78, 81, 85; 324/341, 324/663, 684; 73/335.04
See application file for complete search history.

(56) References Cited

U.S. PATENT DOCUMENTS

2008/0262748 A1 * 10/2008 Ossart et al. ................... 702/21

FOREIGN PATENT DOCUMENTS

| EP | 1 085 316 A2 | 3/2001 |
|---|---|---|
| FR | 2 867 279 | 9/2005 |
| GB | 2 329 711 A | 3/1999 |
| WO | WO 01 79828 A1 | 10/2001 |
| WO | WO 2005 085412 A2 | 9/2005 |
| WO | WO 2005 085818 A2 | 9/2005 |
| WO | WO 2006 021691 A | 3/2006 |

OTHER PUBLICATIONS

Cannizzaro et al; On-Line Biomass Monitoring of CHO Perfusion Culture With Scanning Dielectric Spectroscopy, Laboratory of Chemical and Biochemical Engineering, Swiss Federal Institute of Technology (EPFL), CH 1015 Lausanne, Switzerland; published online Sep. 24, 2003; pp. 597-610; (www.interscience.wiley.com).
Asami et al.; Dielectric Analysis of Yeast Cell Growth; Biochemica et Biophysica Acta 1245 (1995); pp. 99-105.
Davey et al.; On the Dielectric Method of Monitoring Cellular Viability; Department of Biological Sciences, University College of Wales, Aberystwyth, Dyfed, U.K.; Pure & Appl. Chem., vol. 65, No. 9, pp. 1921-1926; (1993).

(Continued)

*Primary Examiner* — John H Le
(74) *Attorney, Agent, or Firm* — Greer, Burns & Crain, Ltd.

(57) ABSTRACT

A process for on-line and in situ counting of cells in a biological culture medium, including a plurality of steps of measuring the capacitance of the medium or a plurality of steps of measuring the conductance of the medium, at distinct frequencies varying within a predetermined range of measurement frequencies. The process includes an extraction of information on the variation of permittivity due to the β-dispersion in the medium, from the capacitance measurements, and processing of the variation of this information on the variation of permittivity as a function of the frequency, in order to provide information regarding the counting of cells in the medium.

21 Claims, 4 Drawing Sheets

OTHER PUBLICATIONS

Archer et al,; Electrorotation Studies of Baby Hamster Kidney Fibroblasts Infected with Herpes Simplex Virus Type 1; Biophysical Journal, vol. 76, May 1999; pp. 2833-2842.

Davey et al.; On the Dielectric Properties of Cell Suspensions at High Volume Fractions; Bioelectrochemistry and Bioenergetics, 28 (1992) 319-340; A section of J. Electroanal. Chem., and constituting vol. 343 (1992); Elsevier Sequoi S.A., Lausanne.

Nicholson et al.; Deconvolution of the Dielectric Spectra of Microbial Cell Suspensions Using Multivariate Calibration and Artificial Neural Networks; Bioelectrochemistry, and Bioenergetics 39 (1996) pp. 185-193.

Yardley et al.; Correction of the Influence of Baseline Artefacts and Electrode Polarisation on Dielectric Spectra; Bioelectrochemistry 51 (2000); pp. 53-65.

Bordi et al.; Reduction of the Contribution of Electrode Polarization Effects in the Radiowave Dielectric Measurements of Highly Conductive Biological Cell Suspensions; Bioelectrochemistry 54; (2001) pp. 53-61.

Harris et al.; Dielectric Permittivity of Microbial Suspensions at Radio Frequencies: A Novel Method for the Real-Time Estimation of Microbial Biomass; Enzyme Microb. Technol. 1987, vol. 9; Mar.; pp. 181-186.

Lisin et al.; Time Domain Dielectric Spectroscopy Study of Human Cells. I. Erythrocytes and Ghosts; Biochimica et Biophysica Acta; 1280 (1996); pp. 34-40.

Carvell, J.P., "On-line biomass monitoring with scanning radio-frequency impedance spectroscopy" presented at the World Brewing Congress 2004, dated Jul. 24-28, 2004 San Diego California.

"Biomass Monitor 'Model 220' User Manual", published Jan. 12, 2004.

"Biomass Monitor 'Model 200' User Manual", by Jeff Davis, Aber Instruments Ltd., published in 2006.

* cited by examiner

PROCESS AND SYSTEM FOR ON-LINE AND IN SITU COUNTING OF CELLS IN A BIOLOGICAL CULTURE MEDIUM

1 INTRODUCTION

The present invention relates to a process for on-line and in situ counting of cells in a biological culture medium. It also relates to a system for counting cells implementing this process.

The pharmaceutical and biotechnology industries use recombined animal cells to produce molecules of therapeutic interest in a bioreactor. Among the available measurements for the optimization and successful performance of the reaction, the quantity of biomass is a parameter of fundamental importance. Measurement of the biomass is today indispensable for characterizing the biological culture processes, this biomass parameter is measured during all the cell cultures.

The reference measurement is to count the number of cells by microscopy after staining with trypan blue. The cells are placed in contact with a dye (trypan blue) beforehand, and only the cells which allow the dye to penetrate are considered dead. Thus it is possible to count the living (unstained) cells, the dead cells (stained with the trypan blue), the total number and to deduce from it the percentage of living cells with respect to the total number of cells, or viability.

Many suppliers offer this method and microscopes combined with image processing, to carry out these different counts. These solutions are more or less automated, but measuring is carried out by a sampling of the reactor.

Other off-line methods (with sampling) are used to complement this reference, such as PCV (packed cell volume), counting by "Coulter counter", counting by flow cytometry, measurement of the dry weight, analysis of the quantity of DNA, etc.

In biological culture, the on-line and in situ measurement of the parameters gives a very significant advantage over the measurement of a sample: measurement in real time, automation of the measurement, option of using regulation loop measurement, no risk of contamination associated with sampling.

Thus many suppliers offer on-line and in situ biomass sensors for biological culture. These biomass sensors use optical or capacitive methods.

The optical methods include measurements of light absorbance or attenuation, more generally called turbidity. The turbidity of the culture medium is correlated with the quantity of biomass in suspension. The optical signal measured is correlated with the quantity of particles in suspension or the number of total cells (living and dead).

Certain biomass sensors use backscattering measurements in which the optical signal measured is correlated with the quantity of particles in suspension and with their size. This signal provides information on the total quantity of biomass (living and dead).

In situ microscopy techniques are also used, in which all the cells (living and dead) are counted directly and the number of total cells is accessible.

Among the on-line measurement techniques, the technique of capacitive measurement is the most efficient and attractive method, as the signal obtained relates to the living biomass only. In fact only the living cells are active, divide, or produce the targeted therapeutic molecules, these are the ones which it is desired to measure first and foremost. This technique provides measurements which are sensitive both to the number and the size of the living cells.

However, no on-line measurement is capable of measuring both the number (independently of changes in the size of the cells) and at the same time the size of the cells such as the off-line reference measurements described above.

2 SUBJECT OF THE INVENTION

The subject of the invention is to propose a counting process which would be implemented in a sensor, on-line and in situ, for the measurement of biomass in biological culture, this sensor being capable of measuring the number of living cells and their size, the number of total cells, and the percentage of living cells with respect to the total number of cells, or viability.

3 STATE OF THE ART

For a disclosure of the basic theory on capacitive measurement of biological cultures, reference can usefully be made to the work (Pethig and Kell 1987; Foster and Schwan 1989; Markx and Davey 1999).

Reference is made in particular to the relationship linking permittivity and excitation frequency, in a measurement of the permittivity of a medium of cells in suspension.

The measurement of capacitance in a cell culture medium, consists firstly of applying a plurality of excitation frequencies comprised between 0.1 and 20 MHZ, and measuring the permittivity at each frequency. The spectrum obtained contains three types of information which are superposed:
  The permittivity due to the β-dispersion of the cells
  The permittivity due to the polarization of the electrodes
  The parasitic permittivity of the electronics The drop in permittivity, caused by the accumulation of a double layer of ions close to the surface of the electrodes, is called the polarization of the electrodes. The drop in permittivity is caused by the polarization of the cellular membranes. This drop in permittivity is called β-dispersion, with reference to FIG. 1.

The β-dispersion can itself be described by three parameters:
  the β-dispersion amplitude, $\Delta\epsilon$
  the characteristic frequency fc,
  the Cole-Cole coefficient $\alpha$.

It is well known by a person skilled in the art that the permittivity due to the β-dispersion contains information on the cells in suspension such as: the number of cells, the average radius, the membrane capacity Cm of the cells, and the conductivity of the cytoplasm.

In order to extract this information on the cells from the capacitive measurements, the most usual method consists of a two-step process:
  Correction: removal of the polarization of the electrode and the parasitic permittivity of the electronics in the measured permittivity spectrum in order to obtain the β-dispersion spectrum.
  Extraction of the radius and the number of cells from the corrected β-dispersion.
Several method variants exist for these two steps.

For the First Step

Correction of the polarization based on the permittivity measurement in the low-frequency region where the contribution of the β-dispersion to the total permittivity is low (typically <500 kHz). [Cannizzaro 2003, Asami 1995]. These methods are based on the hypothesis that the β-dispersion is constant at low frequencies. For large size cells, this hypothesis is no longer valid and this method introduces correction errors.

Bordi [Bordi 2001] has proposed an overall method which determines the contribution of the polarization of the electrodes of the type: $C_p = P \times f^{-pp}$, where P is the amplitude of the polarization, f is the frequency, and $1 < pp \leq 2$. This method does not rely on any hypothesis on the form of the β-dispersion in relation to the measured frequency range, and it makes it possible to determine both P and pp by a non-linear fit on an equivalent electrical circuit. The model used by Bordi is a complex model which encompasses the three contributions in the measurement of the permittivity:

the contribution due to the β-dispersion of the cells the contribution due to the polarization of the electrodes and the contribution due to noise from the electronics.

This approach requires the simultaneous availability of the real part (conductance) and complex part (capacitance) of the measured permittivity. The frequency range used by Bordi is extremely broad (a few kHz to several hundreds of MHz). This frequency range greatly exceeds the frequency ranges currently used in industrial biological culture applications. Further, this range requires the use of a top-of-the-range laboratory impedance meter, the price and the non-industrial character of which are prohibitive in an industrial biological culture application.

For the second step, there are three approaches:

A first approach consists of extracting the number of cells and the radius directly from the capacitance spectrum. This approach relies on statistical methods such as principal component analysis (PCA), and the partial least squares method (PLS) [Cannizzaro 2003].

This method is operated directly on the spectrum of corrected or gross permittivity, but it is difficult for it to take into account the highly non-linear character of the dependence of cell radius on capacitive measurements. Implementation of these statistical methods is arduous, as it requires a prior step of biological culture called the "calibration" step, where the capacitance measurements are compared to an off-line measurement of the number of cells and their radii.

The calibration cultures must be carried out so that the whole range of cell radii and the range of cell numbers capable of being measured are fully covered by the calibration culture. This calibration is specific to one type of cell, and to a specific culture condition. As soon as one of these two factors changes, a new calibration is necessary. This is a major obstacle to generalizing the method and making it practical for an industrial application.

A method of this type, which implies as many calibrations as there are types of cell, is difficult to implement as an industrial process of on-line counting.

A second approach consists of extracting the parameters by fitting: A Cole/Cole type empirical model is used to describe the β-dispersion. Then, the three parameters describing the β-dispersion, Δε, fc, α are extracted by a non-linear fit. The fit is operated on the data after correction of the low-frequency type polarization [Yardley & al 2000]. Implementation of the fit is a particularly critical step, as the estimated parameters are inaccurate due to the non-linear and unstable character of the model in relation to the Cole/Cole parameters. Generally the fit is carried out by algorithms of the genetic type, neural networks [Nicholson 1996], processes of the "simulation annealing" [Lising 1996], or Levenberg-Marquardt [Davey 1992, Davey 1993] type.

Due to these sequential concatenations, the polarisation correction error produces an error in the parameters Δε, fc and α, especially when large cells size are measured. None of these methods are totally reliable for application to a large range of biological cultures.

These parameters can then be used to estimate the number and size of the cells by calculations. The calculations are based on a spherical cell dispersion model called Pauly-Schwan, details of which will be given below. Most frequently, the membrane capacity Cm of the cells and the conductivity of the cytoplasm are the parameters which must be known in order to estimate the size and number of the cells. These parameters can be estimated by off-line measurements of the electrorotation type [Archner, 1999].

A third approach has been proposed by [Asami 1995], which uses an algebraic formula making it possible to assess the characteristic frequency fc with the measurement of conductance and capacitance at a predefined excitation frequency. The drawbacks of this method are that this determination is dependent on the applied frequency (dependence of order 2) which requires the frequency calibration of the impedance meter used and the applied frequency must be close to fc according to the recommendations of Asimi.

Moreover, this method requires a calibration of the start of the culture (t=0). This assumes that the membrane capacity and the intracellular conductance do not vary during the fermentation.

4 DISCLOSURE OF THE INVENTION

The purpose of the invention is to remedy the drawbacks posed by the counting processes of the prior art, both in terms of industrial exploitability and taking account polarization errors.

This aim is achieved with a process for on-line and in situ counting of cells in a biological culture medium, comprising the following steps:

a plurality of measurements of the capacitance of said medium or a plurality of measurements of the conductance of said medium, at different frequencies varying within a predetermined range of measurement frequencies, an extraction of information on the variation in permittivity due to the β-dispersion in said medium, from said capacitance measurements, and processing of said information on the variation of permittivity in order to provide information regarding the counting of cells in said medium.

This process is based on a method making it possible to estimate the average size of the cells and the counting of the cells by dielectric and conductance measurements with several frequencies.

Unlike statistical methods, the counting process according to the invention amounts to combining, in an unexpected manner, the Cole/Cole-type empirical model and a Pauly-Schwan-type model describing the dispersion of a spherical cell.

The main advantage of this invention lies in its precision and its reliability for measurement with all types of biological cells and under all environmental measurement conditions. Unlike the Bordi method, the systemic errors relating to the electronics and polarisation are subjected to a pre-processing, which then simplifies the resolution of the β-dispersion parameters.

In an advantageous version, the process of counting according to the invention comprises moreover a prior step of calibration of a culture of said cells, called the calibration culture, this calibration step comprising:
- (i) at least one plurality of measurements of the permittivity of said calibration culture at predetermined frequencies,
- (ii) processing of said permittivity measurements in order to calculate factors for the determination of the counting information.

Another advantage of the process according to the invention therefore resides in the fact that the implemented method requires no prior knowledge of the membrane capacity Cm of the cells and its cytoplasm conductivity. Instead, for each type of culture, it makes use of a self-calibration procedure which requires only a few specific points (one to three in a preferred embodiment described below) of the calibration culture. The self-calibration consists of correlating these points with an independent measurement of the size and number of the cells.

Within the framework of the process for counting living cells according to the invention, a prior culture—called a calibration culture—is realized, prior culture in which several permittivity spectra (one to three in the preferred embodiment) at a multitude frequencies and the absorbance are measured to determine:
- a factor $\overline{K}_1$ or the constants (a, b, c) which makes it possible to determine the radius in the subsequent cultures with the measurement of critical frequency fc,
- a factor $\overline{K}_2$ or the constants (d, e, f) which makes it possible to determine the number of cells in the subsequent cultures using the measurement of $\Delta\epsilon$ or $\Delta\sigma$ and of the critical frequency fc,
- a factor K' which makes it possible to determine the number of total cells in the subsequent cultures using the measurement of absorbance.

The measurements of the total number of cells and the number of living cells in the subsequent cultures will be used to determine the cell viability.

The constants $\overline{K}_1$, $\overline{K}_2$, or a, b, c, d, e, f, correspond to two preferred embodiments described below.

The estimation of the number and size of the living cells is carried out in two steps:
1. Determining the parameters of the β-dispersion: the amplitude $\Delta\epsilon$ of the dispersion of the capacitances or the amplitude $\Delta\sigma$ of the dispersion of the conductances; the characteristic frequency fc, and optionally the Cole-Cole coefficient α.
2. Estimation of the size and number of the living cells, from these parameters.

According to another aspect of the invention, a system is proposed for on-line and in situ counting of cells in a biological culture medium, implementing a process according to the invention, this system comprising:
- means for measuring the capacitance of said medium, at distinct frequencies varying within a predetermined range of measurement frequencies,
- means for extracting information on the variation of permittivity due to the β-dispersion in said medium, from said capacitance measurements, and
- means for processing said information on the variation of permittivity, in order to provide information on the counting of cells in said medium.

The counting system according to the invention can moreover advantageously comprise means for carrying out a calibration of a culture of said cells, called calibration culture, comprising:
- (i) means for carrying out measurements of the permittivity of said calibration culture at predetermined frequencies,
- (ii) means for processing said permittivity measurements, arranged so as to calculate factors for the determination of the counting information.

5. DETAILED DESCRIPTION OF THE INVENTION

Other advantages and characteristics of the invention will become apparent on examination of the detailed description of an embodiment which is in no way limitative, and the attached drawings in which.

Figure 1:
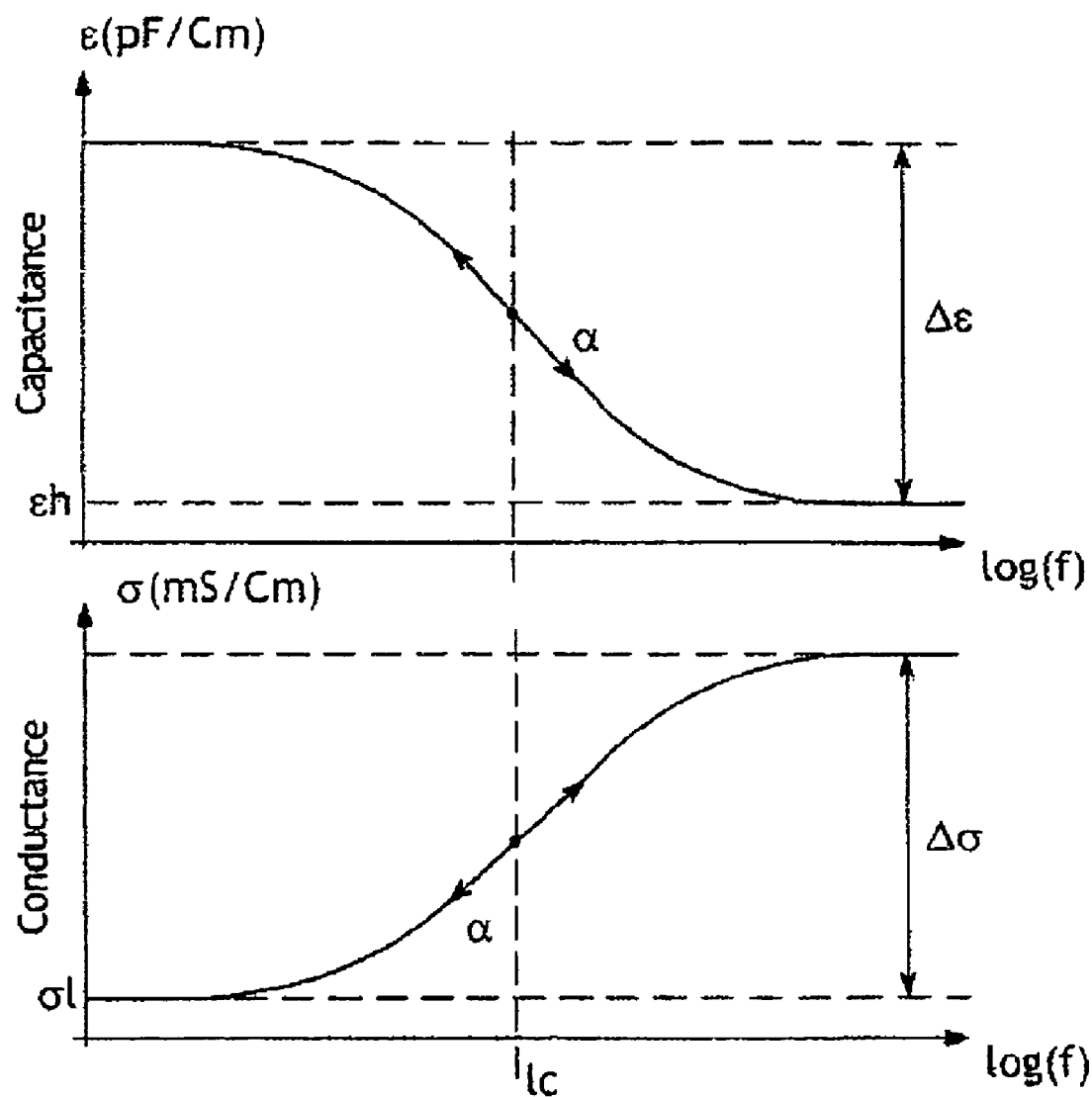
FIG. 1 shows the known phenomenon of β-dispersion in the form of permittivity and conductivity development as a function of frequency.

The different phases of the determination of parameters carried out during the implementation of the counting process according to the invention will now be described.

5.1 Description of the Estimation of the Number of Living Cells from Cole/Cole Parameters An increasing number of cells or a modification in the size of the cells has an influence on the biovolume and on the amplitude of the permittivity signal, according to the first Pauly-Schwan equation:

$$\Delta\varepsilon = \frac{9 \times r \times P \times C_M}{4} \quad (1)$$

with
$\Delta\epsilon$: permittivity (F m$^{-1}$), amplitude of the β-dispersion
r: cell radius (m)
P: volume fraction of the cells (biovolume)

$$P = \frac{4}{3} \times \pi \times r^3 \times Nv \quad (2)$$

Nv: density of living cells (m$^{-3}$)
$C_M$: Membrane capacitance per unit of surface area $$\left(\frac{F}{m^2}\right)$$

The result is that a higher cell radius r has the effect of increasing the amplitude $\Delta\epsilon$ when the volume fraction P (biovolume) remains constant.

The characteristic frequency fc is defined by the second Pauly-Schwan equation:

$$f_c = \frac{1}{2 \times \pi \times r \times C_M \times \left(\frac{1}{\sigma_c} + \frac{1}{2\sigma_m}\right)} \quad (3)$$

with $\sigma_c$: cytoplasm conductivity $\left(\frac{mS}{cm}\right)$ $\sigma_m$: conductivity of the medium $\left(\frac{mS}{cm}\right)$ This critical frequency fc is consequently a function of the size (r) of the cell, the state of the cell and the properties of the cellular membrane $C_M$.

The β-dispersion is the sum of the all of the small β-dispersions generated by each separate cell. The Cole-Cole parameter α represents the distribution of the small β-dispersions at the critical frequency fc.

The two Pauly-Schwan equations describe the two β-dispersion parameters as a function of the four cellular parameters: r, $N_v$, $\sigma_M$, $\sigma_C$.

Under the biological culture conditions frequently encountered, two hypotheses can be assumed:

the membrane capacitance Cm is a known function of the temperature and of the conductivity of the culture medium, The intracellular conductivity σi is a known function of the temperature and of the conductivity of the culture medium.

$$C_M = g(T, \sigma_m) \quad (4)$$

$$\sigma_c = h(T, \sigma_m) \quad (5)$$

Combining these two equations (4) and (5) with the second Pauly-Schwan equation (3), the following is obtained:

$$r = \frac{1}{2\pi} \times \frac{1}{g(T, \sigma_m)} \times \frac{2\sigma_m h(T, \sigma_m)}{2\sigma_m + h(T, \sigma_m)} \times \frac{1}{fc} \quad (6)$$

This equation (6) can be rewritten in a simplified form as follows:

$$r = k_1(T, \sigma_m) \times \frac{1}{fc}, \quad (7)$$

with $$k_1(T, \sigma_m) = \frac{1}{2\pi} \times \frac{1}{g(T, \sigma_m)} \times \frac{2\sigma_m h(T, \sigma_m)}{2\sigma_m + h(T, \sigma_m)}. \quad (7.a)$$

Combining the 1st Pauly-Schwan equation (1), the volume fraction equation (2) with the two equations (4) and (5), the number of living cells is given by:

$$N_V = \frac{16\pi^3}{3} g(T, \sigma_m)^3 \left(\frac{2\sigma_m + h(T, \sigma_m)}{2\sigma_m h(T, \sigma_m)}\right)^4 \times (\Delta\varepsilon \times f_c^4) \quad (8)$$

This equation (6) can be rewritten in a simplified form as follows:

$$N_V = k_2(T, \sigma_m) \times (\Delta\varepsilon \times f_c^4) \quad (9)$$

with $$k_2(T, \sigma_m) = \frac{16\pi^3}{3} g(T, \sigma_m)^3 \left(\frac{2\sigma_m + h(T, \sigma_m)}{2\sigma_m h(T, \sigma_m)}\right)^4. \quad (9.a)$$

The number of living cells is also expressed as a function of the conductance difference Δσ and the frequency fc. In fact, since Δσ=2π*fc*Δε, (9), Nv is calculated in a different manner as follows:

$$N_V = \frac{1}{2\pi} \times k_2(T, \sigma_m) \times (\Delta\sigma \times f_c^3). \quad (10)$$

By combining equations (7) and (9), or (7) and (10), it is established that the determination of Δε and fc, or Δσ and fc allows a direct and on-line measurement of the number of living cells after determination of the functions $k_1$ and $k_2$ by a previously prepared culture and the correlation with a countermeasure of the number of living cells, for example the reference method cited above.

For this purpose, the functions k1 and k2 can be restricted only to a weighted sum of n base functions $\kappa_i$:

$$k_1(T, \sigma_m) = \sum_{i=1,\ldots n} c_i \times \kappa_i(T, \sigma) \quad (11)$$

$$k_2(T, \sigma_m) = \sum_{i=1,\ldots n} d_i \times \kappa_i(T, \sigma). \quad (12)$$

Coefficients $c_i$ and $d_i$ are determined with a calibration culture and by correlating the results given by (7) and (9) or (7) and (10) with at least n results of off-line measurement by a linear regression method.

Once the calibration has been carried out, i.e. once the coefficients $c_i$ and $d_i$ are determined, the sizes and numbers of living cells can be estimated in situ by the capacitive measurements, the temperature and the conductance of the medium with formulae (7) (9) (11) (12), or (7) (10) (11) (12).

If the membrane capacity Cm of the cells and the conductivity of the cytoplasm $\sigma_c$ are known, the equations (7.a) and (9.a) are used in place of (11) (12) during the in situ measurement, and no reference culture is required.

The Cole/Cole parameter α optionally supplies qualitative information on the dispersion of the size of the cells around its average value estimated by (7). An empirical formula is used making it possible to link α and the average radius r and the standard deviation of the size dispersion.

Preferred embodiments for this calibration step will now be described.

1. In a first embodiment, one starts from the fact that it is demonstrated experimentally that for the majority of cultures, the two functions $k_1$ and $k_2$ are not very dependent on the temperature and the conductivity of the medium. These two functions can be successfully approximated by linear functions of the type:

$k_1(T, \sigma_m) = a + b \times T + c \times \sigma_m$ and $k_2(T, \sigma_m) = d + e \times T + f \times \sigma_m$.

Coefficients a, b, c, d, e, f are determined with a minimum of three reference culture experiments in the experience plane (T,$\sigma_m$), and then by carrying out a correlation with a countermeasure of the number of living cells, for example the reference method cited above.

2. In a second embodiment corresponding to a calculation which is a little less accurate of the functions $k_1$ and $k_2$, but much more practicable to calibrate, is approximating them by two constants $\overline{k}_1$ and $\overline{k}_2$ for biological culture applications for which the variation in temperature and conductivity of the medium are negligible:

$$k_1(T,\sigma_m) = \overline{k}_1 \text{ and } k_2(T,\sigma_m) = \overline{k}_2$$

A single measurement of the reference culture is sufficient to characterize the constants $\overline{k}_1$ and $\overline{k}_2$, and correlating them with a countermeasure of the number of living cells, for example the reference method cited above. The temperature and conductance measurement is not necessary in the case of this present preferred embodiment.

5.2 Description of the Determination of the Cole/Cole Parameters from the Measured Spectra Two alternative methods are proposed for determining the β-dispersion parameters necessary for the counting of living cells:

Determination of Parameters α, fc, Δε by the Fitting Method

This determination is carried out in two steps:

Correction of the parasitic permittivity of the electronics and of the systematic polarisation of the electrodes by subtraction; Correction of the parasitic conductance of the electronics by subtraction according to the process Correction of the permittivity due to the residual polarisation of the electrodes and determination of the Cole/Cole parameters themselves by fitting.

Firstly, the permittivity and the conductance due to the electronics are subtracted as follows:

$$\varepsilon^{corr}(f,\sigma_m) = \varepsilon^{mes}(f,\sigma_m) - \varepsilon^{col}(f,\sigma_m) \quad (13)$$

$$\varepsilon^{corr}(f) = \sigma^{mes}(f) - \sigma^{col}(f) \quad (14).$$

The permittivities $\varepsilon^{col}(f)$ and the conductances $\sigma^{col}(f)$ are measured by the probe in a medium without cells, of the same conductance $\sigma_m$ at low frequency as during the measurement of the culture with cells. Unlike [Bordi 2001]. This correction makes it possible to eliminate the contribution of parasitic capacitances due to the electronics in the measured permittivity.

The corrected permittivities measured for a plurality of frequencies {f} are then fitted by a Cole/Cole model, and increased by a random polarisation term:

$$\varepsilon(f) = \Delta\varepsilon \times \frac{1 + rf^{1-\alpha}\sin(\alpha\pi/2)}{1 + rf^{2(1-\alpha)} + 2 \times rf^{1-\alpha}\sin(\alpha\pi/2)} + \varepsilon_h + \Delta P \times f^{-pp}, \quad (15.a)$$

$$\sigma(f) = \Delta\sigma \times \frac{rf^{2-\alpha}\cos(\alpha\pi/2)}{1 + rf^{2(1-\alpha)} + 2 \times rf^{1-\alpha}\sin(\alpha\pi/2)} + \sigma_l, \quad (15.b)$$

with $$rf := \frac{f}{fc}.$$

The five parameters to be determined are:
α: Cole/Cole parameter,
Δε: amplitude of the permittivity dispersion,
$f_c$: characteristic frequency,
ΔP: amplitude of the residual polarization,
$\varepsilon_h$: baseline, limit of the capacitance when the frequency tends towards infinity.

The two other parameters are:
Δσ: amplitude of the conductance dispersion,
$\sigma_l$: baseline, the low-frequency conductance pp is a constant called polarization power. The value of this constant—comprised between 1 and 2—is specific to each probe (in particular depending on its geometry and the porosity of its electrodes), and it is characterized for the probe once only.

The fit calculation is carried out in a processing unit, by seeking to minimize a function of the weighted "least squares" distance between the model (15.a) and the corrected data (13):

$$J(\alpha, \Delta\varepsilon, f_c, \Delta P, \varepsilon_h) = \sum_f w(f) \times (\varepsilon^{corr}(f) - \varepsilon(f))^2.$$

The weighting coefficients w(f) are introduced to compensate the difference in behaviour of the electronic noise as a function of the excitation frequency.

In a preferential embodiment of the method, the algorithm based on a variant of a Quasi-Newton, Broyden-Fletcher-Goldfarb-Shanno (BFGS) type algorithm with limited memory with preconditioning, is used to minimize J.

The variant introduced within the framework of the present invention is a modification of the standard BFGS algorithm for the purpose of restricting the parameters in their validity ranges: $1 < \alpha \leq 2$, $\Delta\varepsilon \geq 0$, $f_c > 0$.

According to the type of biological culture, other restrictions involving the parameters of the Cole/Cole model can be added to the algorithm in order to make it more stable.

In another variant of the method, the real part of the permittivity according to the Cole/Cole dispersion model (15.b) is combined with the imaginary part shown in (15.a) to form a complex permittivity model used by the fit.

This model is fitted for both corrected conductance and capacitance measurements (13) and (14). Δσ and $\sigma_l$ are added to the list of fit parameters. This combination increases the precision in determining the Cole/Cole parameters.

Determination of the Parameters α, fc, Δσ by the Algebraic Method

Statistical methods of the PLS type or by linear regression present the drawbacks of (i) requiring the use of a large frequency range for describing the β-dispersion, and (ii) using computation-heavy algorithms. This makes the task of integration into electronic chips difficult.

The algebraic method has the advantage of being very easily installed into an integrated circuit as it is very undemanding in terms of computing power and in terms of frequency use. It does not use linear regression and does not require a minimal number of measurement frequencies.

The parameters α, fc, Δσ are determined by the algebraic resolution of physical models of cell behaviour.

The state of the art prompts the use of capacitance spectroscopy for determining the characteristic parameters α, fc, Δε. Now, the conductance is also affected by this dispersion.

The method consists of combining the β dispersion models of the conductance and capacitance in order to determine algebraically the characteristic parameters α, fc, Δσ.

This method is preferably used starting from simplified Pauly and Schwan expressions when α=0:

$$\varepsilon(f) = \varepsilon_h + \frac{\Delta\varepsilon}{1+\left(\frac{f}{fc}\right)^2} \quad (16)$$

$$\sigma(f) = \sigma_l + \frac{\Delta\sigma\left(\frac{f}{fc}\right)^2}{1+\left(\frac{f}{fc}\right)^2} \quad (17)$$

$$\Delta\sigma = 2\pi * fc * \Delta\varepsilon \quad (18)$$

The characteristic frequency fc is therefore obtained by combining the expressions (16) (17) and (18)

$$fc = \frac{1}{2\pi} * \frac{\sigma(f1) - \sigma(f2)}{\varepsilon(f1) - \varepsilon(f2)} \quad (19)$$

With only at least two frequencies, it is therefore possible to determine the frequency fc.

The result of the combination of equations (16) (17) and (18) is not restricted to this form only, and it can be modified so as to use several frequencies.

It is also apparent that contrary to all the other known methods, this determination of fc is independent of all the other parameters of the medium in suspension: the radius r, the membrane capacity Cm, the intra-cell conductivity, the bio volume P, the conductivity of the medium.

This determination of the characteristic frequency fc is also independent of the chosen frequencies. The result is that the precision at which the frequencies f1 and f2 are applied is unimportant, unlike the methods which use only the capacitance spectroscopy. This has the advantage of dispensing with frequency calibration of the impedance metre used.

Moreover, the corresponding mathematical relationship for calculation of the characteristic frequency fc is very easy to implement in an integrated circuit.

A practical mode for determining the variation in conductance Δσ will now be described. This variation is obtained algebraically in different ways, starting from the use of the equation (17)

$$\Delta\sigma = (\sigma(f) - \sigma l)\left(\left(\frac{fc}{f}\right)^2 + 1\right)$$

A single measurement frequency can be used if σl is negligible in comparison to Δσ.

In the more common case, at least two frequencies are used for determining Δσ algebraically.

A practical mode for determining the viability of the cells will now be described, within the framework of the counting process according to the invention.

As described above, the measurement of light absorbance or attenuation, more generally called turbidity, is correlated with the quantity of biomass in suspension. The measured optical signal is correlated with the quantity of particles in suspension or with the number of total cells (living and dead).

Absorbance=$K'*Nt$

With Nt=number of total cells

Determination of the absorbance is a direct and on-line measurement of the number of total cells after determination of K' using a prior culture and the correlation with a countermeasure of the number of total cells, for example the reference method cited above.

The cell viability is determined by the following expression:

$Nv*100/Nt$=Cell viability

The measurements of the number of total cells and of the number of living cells in the subsequent cultures will be used to determine the cell viability.

With reference to the above mentioned figures, an example of the implementation of the counting process according to the invention will now be described, at the same time as a counting system implementing this process.

Figure 2:
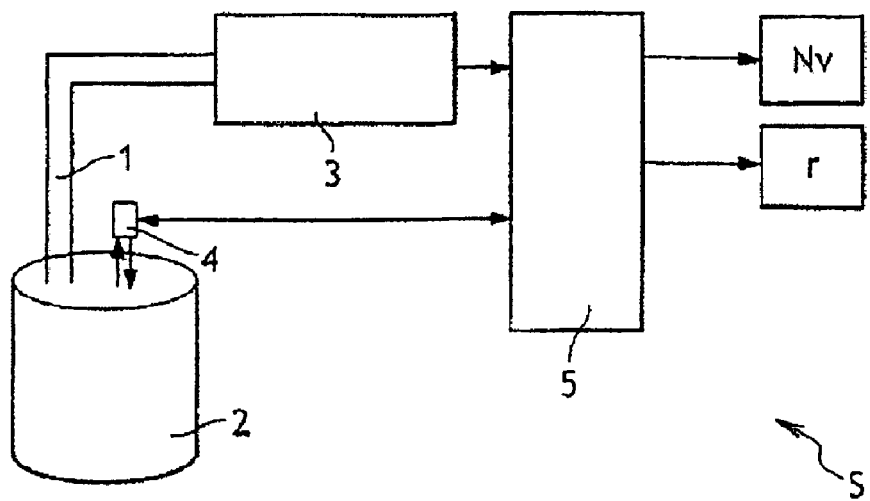
FIG. 2 is a block diagram of a system for counting cells according to the invention.

A system S for counting cells comprises, with reference to FIG. 2:

- a device with capacitive electrodes 1 immersed in a cell suspension inside a fermenter 2,
- an electronic control unit 3, comprising for example a floating bridge and designed to generate a variable excitation frequency and to generate a capacitance signal,
- a processing unit 5 for extracting from this capacitance signal which varies as a function of the frequency, information relating to the β-dispersion of the medium, in particular the critical frequency fc, the permittivity variation Δε, and to provide an on-line measurement of the number of living cells and optionally the average radius of these cells,
- an optical cell 4 for measuring the absorbance of the medium.

Figure 3:
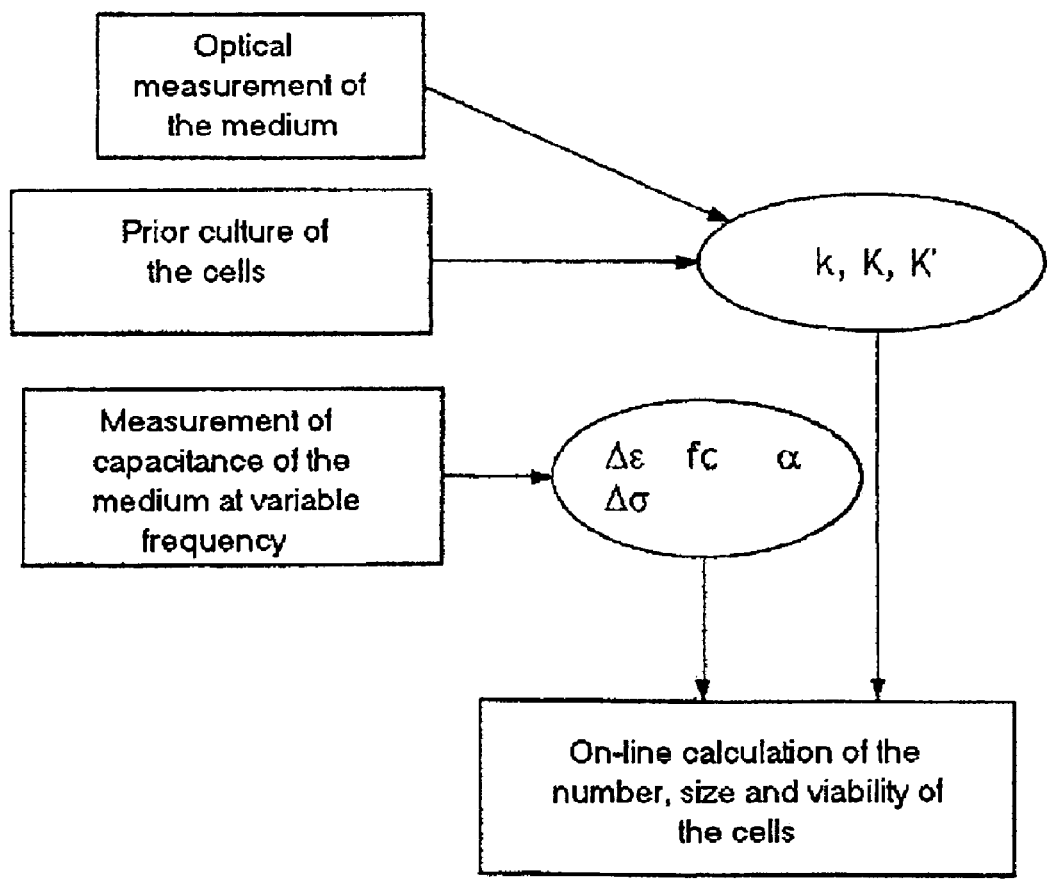
FIG. 3 shows the steps of the process for counting cells according to the invention.
Figure 4:
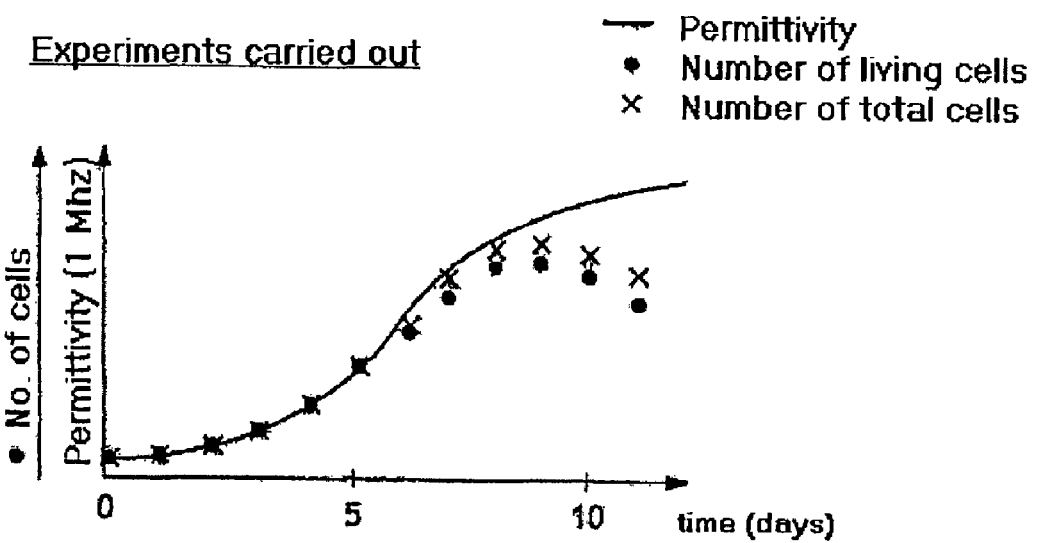
FIG. 4 shows a development of the number of living cells and total cells respectively in a medium and of the permittivity as a function of time.
Figure 5:
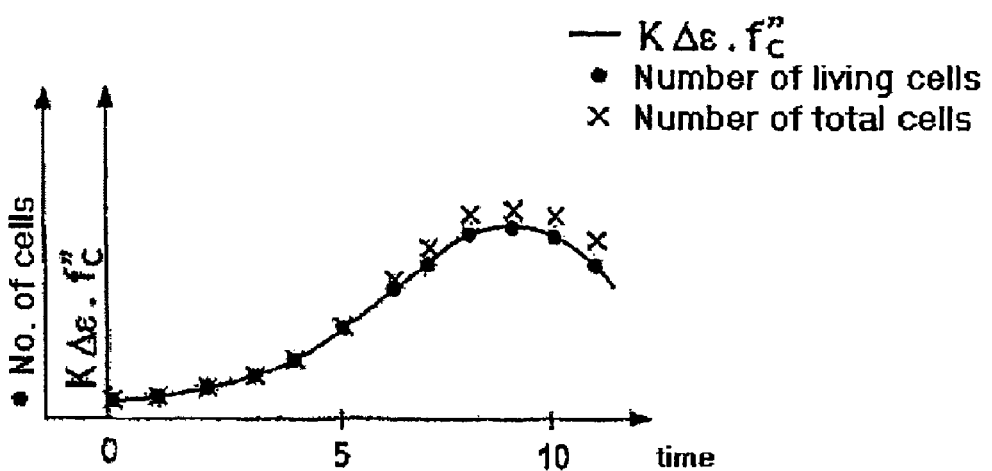
FIG. 5 shows a development of the number of living cells and total cells respectively in a medium and of the variation in permittivity as a function of time.
Figure 6:
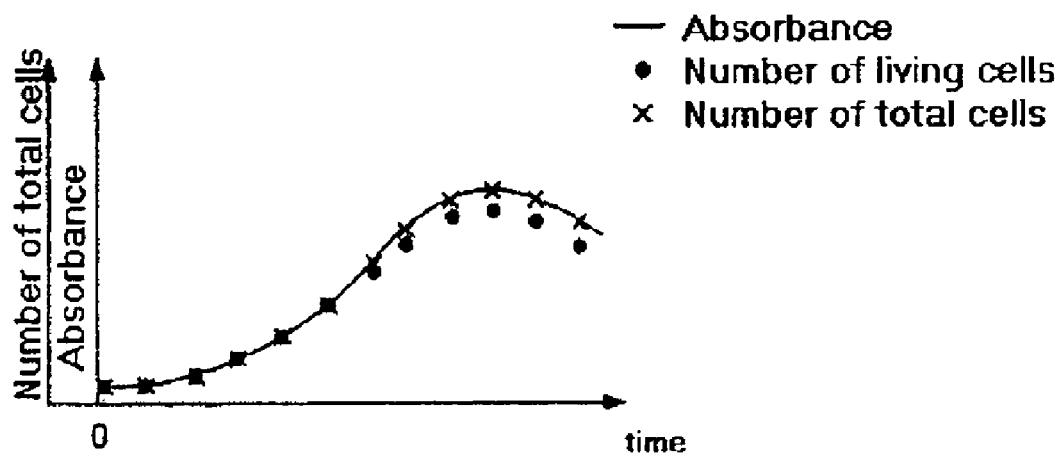
FIG. 6 shows a development of the respective numbers of living cells and total cells and of the absorbance as a function of time.
Figure 7:
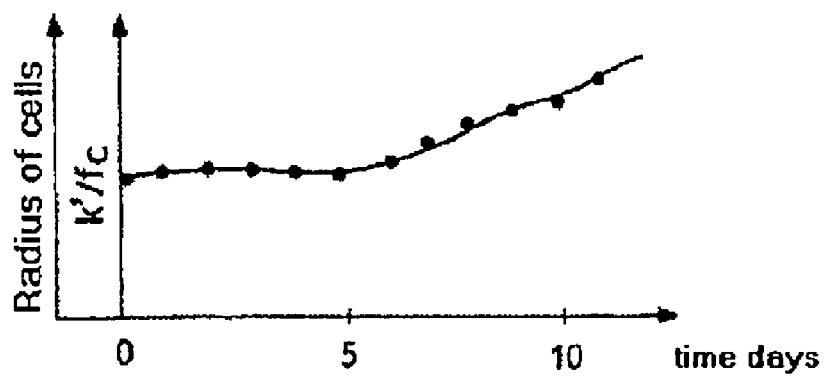
FIG. 7 shows a development of the average radius of cells in a medium as a function of time.

With reference to FIG. 3, the counting process according to the invention is implemented in practice in the form of software for processing physical variables such as capacitance and absorbance. This software is run for processing these absorbance and capacitance measurements which vary as a function of the frequency in order to generate the characteristic parameters of β-dispersion in the medium.

Experimental results are shown in FIGS. 4 to 7.

Of course, the invention is not limited to the examples which have just been described and numerous adjustments can be made to these examples without exceeding the scope of the invention.

The capacitance and (or) conductance signals can thus originate from any type of impedance measurement device (impedance measurement) equipped with frequency scanning and connected to a sensor immersed in a biological medium.

Under the term "impedance measurement" are comprised:

- the various methods of measuring impedance based on the determination of the V/I ratio of a sample to be measured, some of which are described in the book "Impedance Measurement Handbook" published by Hewlett Packard,
- the zero methods such as the one disclosed in the document WO 0 179 828 in the name of the present Applicant,
- the resonance method, and more generally,
- any method making it possible to determine the conductance and capacitance of the biological medium in which is the sensor is immersed.

BIBLIOGRAPHIC REFERENCES

[1] John E. Yardley, Robert Todd, David J. Nicholson, John Barrett, Douglas B. Kell, Christopher L. Davey, Correction of the influence of baseline artefacts and electrode polarisation on dielectric spectra, Bioelectrochemistry 51 (2000) 53-65.

[2] David J. Nicholson, Douglas B. Kell, Christopher L. Davey, Deconvolution of the dielectric spectra of microbial cell suspensions using multivariate calibration and artificial neural networks, Bioelectrochemistry and Bioenergetics 39 (1996) 185-193.

[3] C. L Davey, H. M. Davey and D. B. Kell (1992) On the dielectric properties of cell suspensions at high volume fractions. Bioelectrochemistry and Bioenergetics 28 pp:319-330.

[4] Christopher L. Davey, Gerard H. Mark and Douglas B. Kell. (1993). On the dielectric method of monitoring cellular Viability. Pure &App/. Chern., Vol. 65, NO. 9, pp.: 1921-1926.1993.

[5] Steffen Archer, Hywel Morgan, and Frazer 3. Rixon, Electrorotation Studies of Baby Hamster Kidney Fibroblasts Infected with Herpes Simplex Virus Type 1, Biophysical Journal Volume 76 May 1999 2833-2842.

[6] Christopher Cannizzaro, Raphael Gugerli, Ian Marison, Urs von Stockar, On-Line Biomass Monitoring of CHO Perfusion Culture With Scanning Dielectric Spectroscopy, 24 Sep. 2003 in Wiley InterScience (www.interscience.wiley.com).

[7] Koji Asami, Takeshi Yonezawa, Dielectric analysis of yeast cell growth, Biochimica and Biophysica Acta 1245 (1995) 99-105.

[8] F. Bordi, C. Cametti, T. Gili, Reduction of the contribution of electrode polarization effects in the radiowave electric measurements of highly conductive biological cell suspensions. Bioelectrochemistry 54 (2001), 53-61.

The invention claimed is:

1. A process for on-line and in situ cell counting in a biological culture medium, implemented in a sensor for biomass measurement, the process comprising:
   a plurality of steps of measuring of the capacitance of said medium or a plurality of steps of measuring of the conductance of said medium at distinct frequencies varying within a predetermined range of measurement frequencies;
   extracting information on the variation of permittivity due to the β-dispersion in said medium from said capacitance measurements; and
   processing said information on the variation of permittivity in order to provide information regarding the counting of cells in said medium.

2. The process according to claim 1, characterized in that it comprises moreover a prior step of calibration of a culture of said cells, called the calibration culture, said calibration step comprising:
   (i) at least one plurality of measurements of the permittivity of said calibration culture at predetermined frequencies; and
   (ii) processing of said permittivity measurements in order to calculate factors for the determination of the counting information.

3. The process according to claim 2, characterized in that the prior calibration step moreover comprises an operation of correlation of the permittivity measurements with an off-line measurement enabling the measurement of the total quantity of biomass of the calibration culture used as a reference.

4. The process according to claim 3, characterized in that the optical measurement enabling the measurement of the total quantity of biomass in the calibration culture is arranged so as to provide an optical signal, such as $$\text{absorbance} = K'^* N t$$

wherein Nt=number of total cells and K' is a coefficient.

5. The process according to claim 4, characterized in that the calibration step is arranged so as to determine the coefficient K'.

6. The process according to claim 5, characterized in that it comprises moreover a direct on-line measurement of the number Nt of total cells, starting from the optical signal enabling the measurement of total quantity of biomass measured and the coefficient K' determined during the prior culture step.

7. The process according to claim 6, characterized in that it comprises moreover providing information on cell viability according to the formula:

$$Nv^*100/Nt = \text{Cell viability}$$

wherein Nv is the number of living cells or biovolume and Nt is the number of total cells.

8. The process according to claim 2, characterized in that the prior calibration step is intended to determine a function k corresponding to the product of the radius r of the cells of the medium and the critical frequency fc of the β-dispersion.

9. The process according to claim 8, characterized in that it comprises moreover a step for providing an on-line measurement of the average radius of the cells of the medium, from the determination of the critical frequency fc.

10. The process according to claim 9, characterized in that it comprises moreover a determination of the number of living cells in the medium, from the average radius of a cell determined on-line.

11. The process according to claim 9, characterized in that it comprises moreover a step of direct off-line measurement of the average radius and a step of correlation between the direct measurement and the on-line indirect measurement of said average radius obtained from the on-line determination of the critical frequency fc.

12. The process according to claim 11, characterized in that the direct off-line measurement of the average radius is carried out by microscopy.

13. The process according to claim 1, characterized in that the step of extracting information on a variation of permittivity due to the β-dispersion comprises a determination of descriptive parameters of this β-dispersion, from at least one of the three following parameters: the permittivity variation Δε, the conductance variation Δσ, the critical frequency fc, and the parameter α.

14. The process according to claim 1, characterized in that it comprises moreover a determination of the number of living cells or biovolume according to the formula:

$$Nv = K^* \Delta \epsilon^* fc^4$$

wherein Δε and fc are descriptive parameters of this β-dispersion comprising Δε the permittivity variation and fc the critical frequency and
wherein K is a function.

15. The process of according to claim 14, characterized in that it comprises moreover a prior step of calibration of a culture of said cells, called the calibration culture, said calibration step comprising:
   (i) at least one plurality of measurements of the permittivity of said calibration culture at predetermined frequencies; and (ii) processing of said permittivity measurements in order to calculate factors for the determination of the counting information, and further characterized in that the prior calibration step is arranged so as to determine the function K.

16. The process according to claim 1, characterized in that it comprises moreover a determination of the number of living cells or biovolume according to the formula:

$$Nv = K * \Delta\sigma * fc^3 / 2\pi$$

wherein $\Delta\sigma$ and fc are descriptive parameters of this β-dispersion comprising $\Delta\sigma$ the conductance variation and fc the critical frequency and
wherein K is a function.

17. The process according to claim 1, characterized in that the range of measurement frequencies is comprised between 0.1 and 20 MHz.

18. A system for on-line and in situ counting of cells in a biological culture medium, implemented in a sensor for biomass measurement, the process comprising:
a probe that measures the capacitance of said medium at distinct frequencies varying within a predetermined range of measurement frequencies; and
a processing unit configured to extract information on the variation of permittivity due to the β-dispersion in said medium from said capacitance measurements and processing said permittivity variation information to deliver a cell counting information in said medium.

19. The system according to claim 18, wherein:
(i) said probe measures permittivity of said calibration culture at predetermined frequencies; and
(ii) said processing unit processes said permittivity measurements arranged so as to calculate factors for the determination of the counting information.

20. The system according to claim 18, wherein said processing unit carries out a direct off-line measurement of the average radius of the cells of the medium, and a correlation between said direct measurement and the indirect on-line measurement of said average radius obtained from the on-line determination of the critical frequency fc of said medium.

21. The system according to claim 20, characterized in that it further comprises microscopy equipment configured to perform the direct off-line measurement of the average radius.

* * * * *